(12) United States Patent
Kobayashi et al.

(10) Patent No.: US 7,914,650 B2
(45) Date of Patent: Mar. 29, 2011

(54) AIR FILTERING APPARATUS

(75) Inventors: Masanori Kobayashi, Ashikaga (JP); Mitsuhiro Dobashi, Kumagaya (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 854 days.

(21) Appl. No.: 11/860,690

(22) Filed: Sep. 25, 2007

(65) Prior Publication Data

US 2008/0073204 A1 Mar. 27, 2008

(30) Foreign Application Priority Data

Sep. 26, 2006 (JP) .................................. 2006-261314

(51) Int. Cl.
*C25B 9/04* (2006.01)
*B01F 3/04* (2006.01)
*C25B 1/26* (2006.01)

(52) U.S. Cl. ............... 204/229.5; 204/229.7; 204/228.6; 204/229.2; 204/229.3; 261/115

(58) Field of Classification Search .................. None
See application file for complete search history.

(56) References Cited

U.S. PATENT DOCUMENTS

| 5,616,234 | A | * | 4/1997 | Rhees et al. | .................. 205/500 |
| 5,797,964 | A | * | 8/1998 | Carlson et al. | ..................... 607/2 |
| 6,699,370 | B2 | * | 3/2004 | Kuriyama et al. | ......... 204/157.3 |
| 2004/0065541 | A1 | * | 4/2004 | Sehlin | ......................... 204/228.1 |
| 2007/0017801 | A1 | * | 1/2007 | Fukui et al. | ................ 204/230.2 |

FOREIGN PATENT DOCUMENTS

EP 1788315 A2 * 5/2007
JP 2002-181358 A 6/2002

* cited by examiner

*Primary Examiner* — Harry D Wilkins, III
(74) *Attorney, Agent, or Firm* — Westerman, Hattori, Daniels & Adrian, LLP (57) ABSTRACT

In an air filtering apparatus in which power is supplied from a power supply to electrodes in an electrolytic bath to electrolyze water in the electrolytic bath and thus generate electrolytic water and the generated electrolytic water and air are supplied to a gas-liquid contact member to filter the air, a voltage varying unit varies the voltage applied between the electrodes, and includes a voltage switching unit for switching a power supply voltage, a voltage adjusting unit for adjusting the power supply voltage switched by the voltage switching unit and applying the adjusted voltage between the electrodes and a controller for controlling the voltage switching unit so that the power supply voltage is adjusted to a voltage nearest to the adjusted power supply voltage by the voltage adjusting unit.

7 Claims, 11 Drawing Sheets

AIR FILTERING APPARATUS

INCORPORATION BY REFERENCE

The present application claims priority under 35 U.S.C. §119 to Japanese Patent Application No. 2006-261314 filed on Sep. 26, 2006. The content of the application is incorporated herein by reference in its entirety.

BACKGROUND OF THE INVENTION

1. Field of the Invention

The present invention relates to an air filtering apparatus for supplying power from a power supply to electrodes in an electrolytic bath to electrolyze water in the electrolytic bath and thus generate electrolytic water, and removing microorganisms floating in the air such as bacteria, virus, fungus, etc. (hereinafter merely referred to as "virus, etc.") by using the electrolytic water.

2. Description of the Related Art

There is known a humidifying element for supplying power from a power supply to electrodes in an electrolytic bath to electrolyze water in the electrolytic bath and thus generate electrolytic water containing hypochlorous acid and subjecting sterile filtration to a humidifying element by using the electrolytic water (for example, see JP-A-2002-181358). In this apparatus, a power supply having a power supply switch (using DC 12V to 18V) is connected to the electrodes and the power supply switch is turned on to subject the humidifying element to sterilize filtration during only the time period when water is supplied to the humidifying element until the humidity of a room is equal to a predetermined humidity.

In order to stably generate electrolytic water, it is considered to provide a voltage varying circuit for variably controlling the voltage applied between the electrodes in the electrolytic bath to keep current constant. With respect to this type of voltage varying circuit, in a case where a circuit for adjusting the voltage only by modulating the pulse width is adopted, a radiating device (for example, heat sink) for radiating heat of the power supply circuit containing this voltage varying circuit must be designed in a large size in proportion to the amount corresponding to the voltage drop of the power supply when it is required to secure a sufficient control voltage range, and also thermal loss in the radiating device induces power consumption.

SUMMARY OF THE INVENTION

Therefore, an object of the present invention is to provide an air filtering apparatus in which a radiating device can be miniaturized and also power consumption caused by thermal loss can be reduced.

In order to attain the above object, an air filtering apparatus in which power is supplied from a power supply to electrodes in an electrolytic bath to electrolyze water in the electrolytic bath and thus generate electrolytic water and the generated electrolytic water and air are supplied to a gas-liquid contact member to filter the air, comprising: a voltage varying unit that varies the voltage applied between the electrodes and includes a voltage switching unit for switching a power supply voltage, a voltage adjusting unit for adjusting the power supply voltage switched by the voltage switching unit and applying the adjusted voltage between the electrodes and a controller for controlling the voltage switching unit so that the power supply voltage is adjusted to a voltage nearest to the adjusted power supply voltage by the voltage adjusting unit.

According to this invention, the voltage varying unit for varying the voltage applied between the electrodes is equipped with the voltage switching unit for switching the power supply voltage, the voltage adjusting unit for adjusting the power supply voltage switched by the voltage switching unit and applied the adjusted power supply voltage between the electrodes, and the controller for controlling the voltage switching unit so that the power supply voltage is adjusted to the voltage nearest to the adjusted power supply voltage by the voltage adjusting unit. Therefore, the voltage drop of the voltage adjusting unit can be reduced, a radiating device such as a heat sink or the like can be miniaturized, and the power consumption based on thermal loss can be reduced.

In the above construction, it is preferable that the voltage switching unit switches a resistor connected to the power supply, and outputs the voltage based on the switched resistor, thereby switching the power supply voltage. According to this construction, the power supply voltage is switched by switching the resistor, so that the construction of the voltage switching unit can be simplified.

In this case, the voltage switching unit preferably comprises plural resistance elements, and a switching unit for selectively connecting the plural resistance elements to the power supply under the control of the controller.

Furthermore, in the above construction, the voltage adjusting unit preferably adjusts the power supply voltage switched by the voltage switching unit through pulse width modulation.

Still furthermore, in the above construction, it is preferable that the controller has a detector for detecting the electrical conductivity or resistance value of water in the electrolytic bath, sets target current to flow between the electrodes on the basis of the detection result of the detector, and controls the voltage switching unit and the voltage adjusting unit so that current flowing between the electrodes is converged within a predetermined range based on the target current. According to this construction, the target current to flow through water is set on the basis of the electrical conductivity or resistance value of water. Therefore, even when ion concentration in water varies, the concentration of electrolytic water can be stabilized.

Furthermore, in the above construction, it is preferable that the controller controls the voltage switching unit and the voltage adjusting unit so that the voltage applied between the electrodes is gradually varied when the current flowing between the electrodes is out of the predetermined range based on the target current and then kept to the voltage at the time point when the current flowing between the electrodes enters the predetermined range. According to this construction, the voltage switching unit and the voltage adjusting unit are controlled so that the voltage applied between the electrodes is gradually varied, and when the current flowing between the electrodes enters the predetermined range, the voltage applied between the electrodes is kept to the voltage at that time point. Therefore, the current value flowing between the electrodes can be surely set within the control range by feed-back control.

Still furthermore, in the above construction, it is preferable that the controller controls the voltage switching unit and the voltage adjusting unit so that the voltage applied between the electrodes is equal to the lowest voltage under a condition that the current flowing between the electrodes exceeds the target current and the difference between the current and the target current is equal to a predetermined value or more, and executes alarm processing insofar as the condition concerned is satisfied even after the control. According to this construction, abnormality of the air filtering apparatus can be detected with high precision and reports the abnormality with protecting circuits.

According to the present invention, the voltage varying unit for varying the voltage applied between the electrodes in the electrolytic bath is equipped with the voltage switching unit for switching the power supply voltage, the voltage adjusting unit for adjusting the power supply voltage switched by the voltage switching unit and applying the adjusted voltage between the electrodes, and the controller for controlling the voltage switching unit and the voltage adjusting unit so that the voltage switching unit switches the power supply voltage to the voltage nearest to the power supply voltage after the adjustment of the voltage adjusting unit. Therefore, the voltage drop of the voltage adjusting unit can be reduced, the radiating device such as a heat sink or the like can be miniaturized and the power consumption caused by the thermal loss can be reduced.

DETAILED DESCRIPTION OF THE PREFERRED EMBODIMENTS

Preferred embodiments according to the present invention will be described hereunder with reference to the accompanying drawings.

Figure 1:
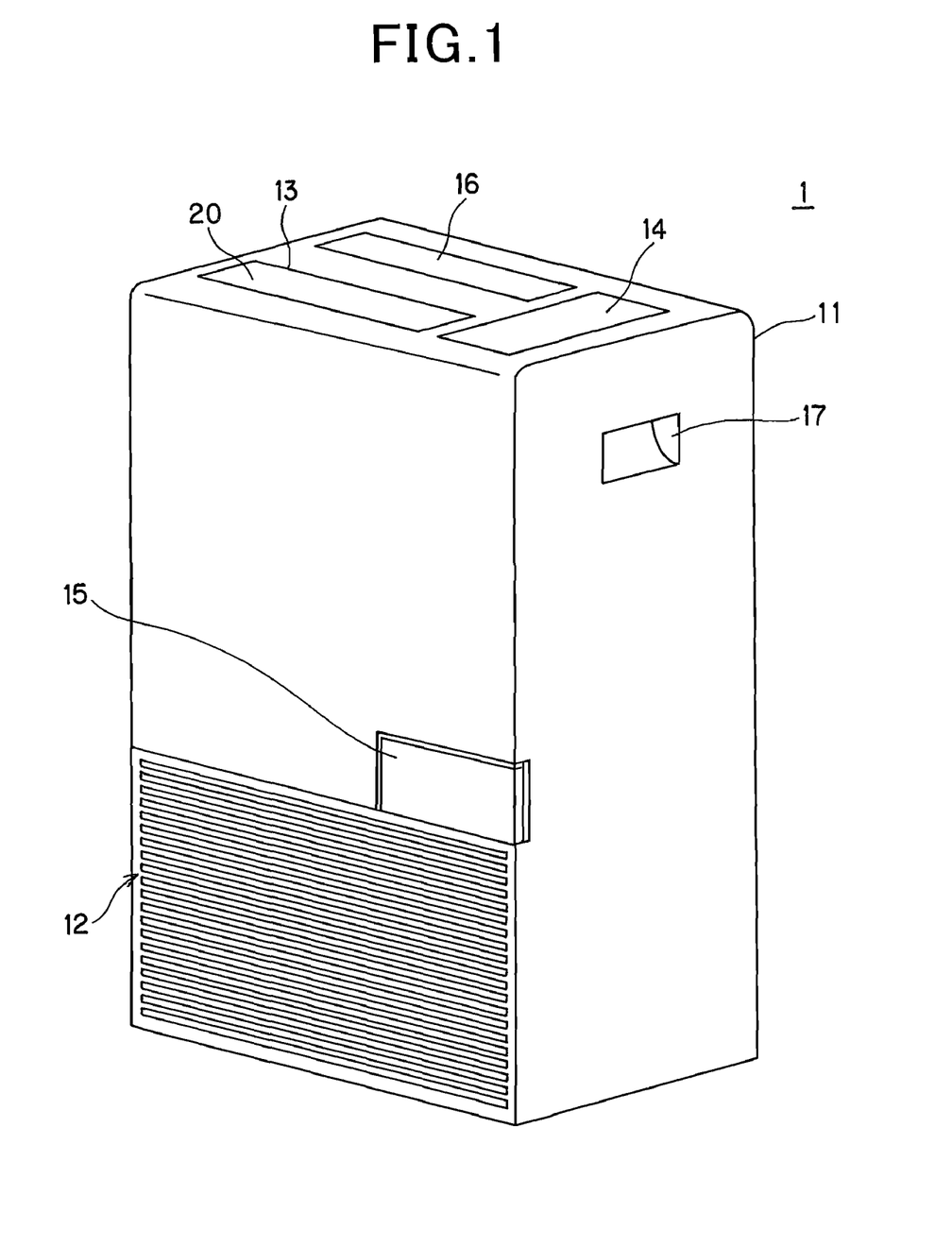
FIG. 1 is a perspective view showing the outlook of an air filtering apparatus according to an embodiment of the present invention.
Figure 2:
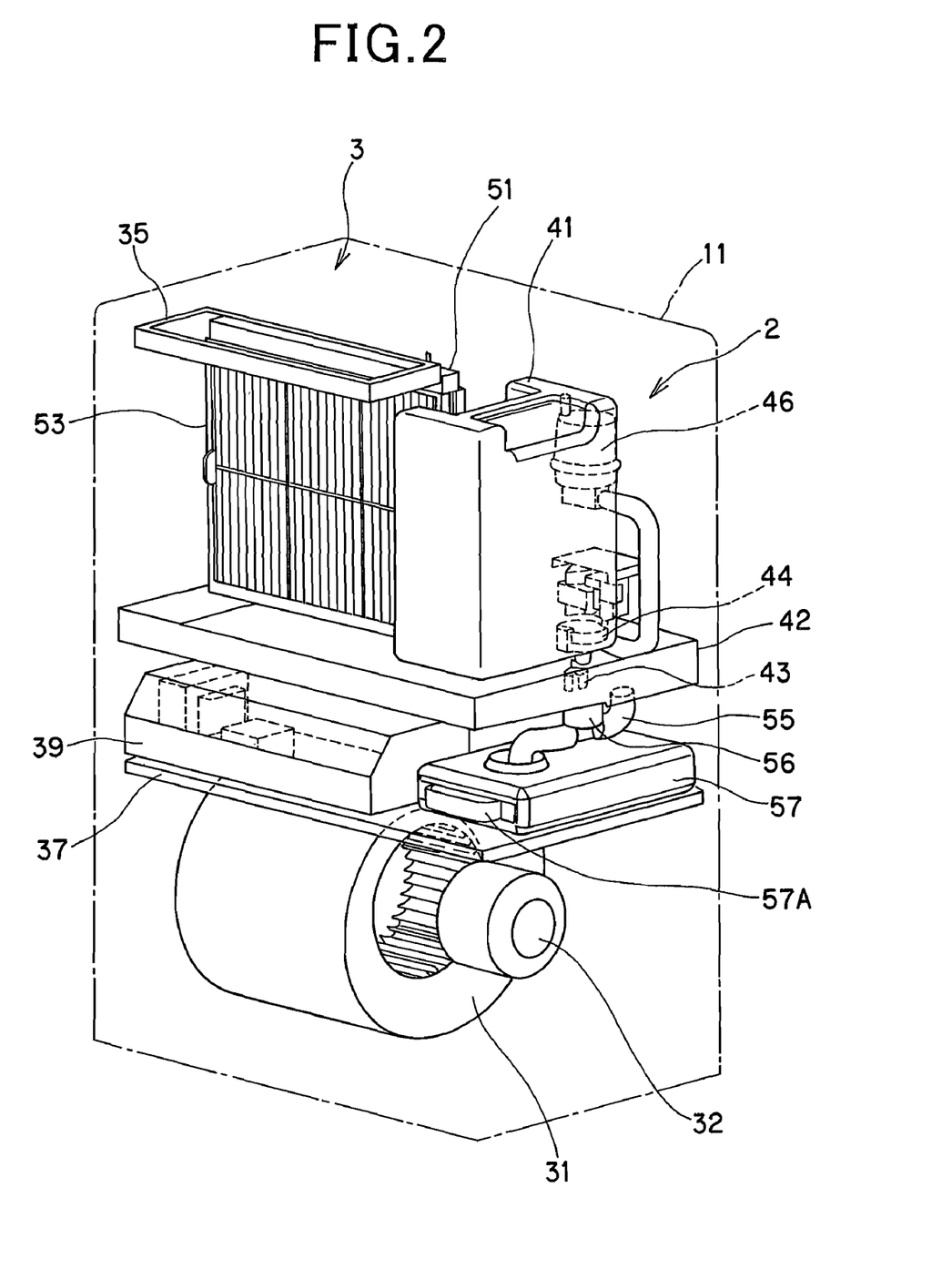
FIG. 2 is a perspective view showing the internal construction of the air filtering apparatus.

FIG. 1 is a perspective view showing the outlook of an air filtering apparatus 1 according to an embodiment to which the present invention is applied, and FIG. 2 is a perspective view showing the internal construction of an air filtering apparatus 1. In FIG. 2, the outlook of a housing 11 is illustrated by a virtual line for reference.

As shown in FIG. 1, the air filtering apparatus 1 has a vertically long box-shaped housing 11, and it is set on the floor, for example. An suction grille 12 is provided to the lower portion of the front face of the housing 11, and an air blow-out port 13 as an exhaust port is provided to the top face of the housing 11. A louver 20 for changing the air blowing direction of air is provided to the air blow-out port 13.

The air filtering apparatus 1 sucks and filters air through the suction grille 12 from a room where the air filtering apparatus is set, and blowing out the filtered air from the air blow-out port 13 into the room, thereby cleaning the indoor air.

The top face of the housing 11 is equipped with an operation panel 16 for carrying out various kinds of operations of the air filtering apparatus 1, and a water supply tank take-out port 14 through which a water supply tank 41 (FIG. 2) described later is inserted or taken out. An openable and closable lid is secured to the water supply tank take-out port 14. Furthermore, the front face of the housing 11 is equipped with a drain receiver take-out port 15 through which a drain receiver 57 (FIG. 2) described later is inserted and taken out, and an openable and closable lid is secured to the drain receiver take-out port 15.

A grip portion 17 is formed at each of the upper portions of both the side faces of the housing 11. These grip portions 17 are recess portions (handholds) on which user's hands put when the housing 11 is lifted by hands. Accordingly, a user can lift and move the air filtering apparatus by himself/herself while carrying the air filtering apparatus.

Next, the internal construction of the air filtering apparatus 1 according to this embodiment will be described with reference to FIGS. 2 to 6

Figure 3:
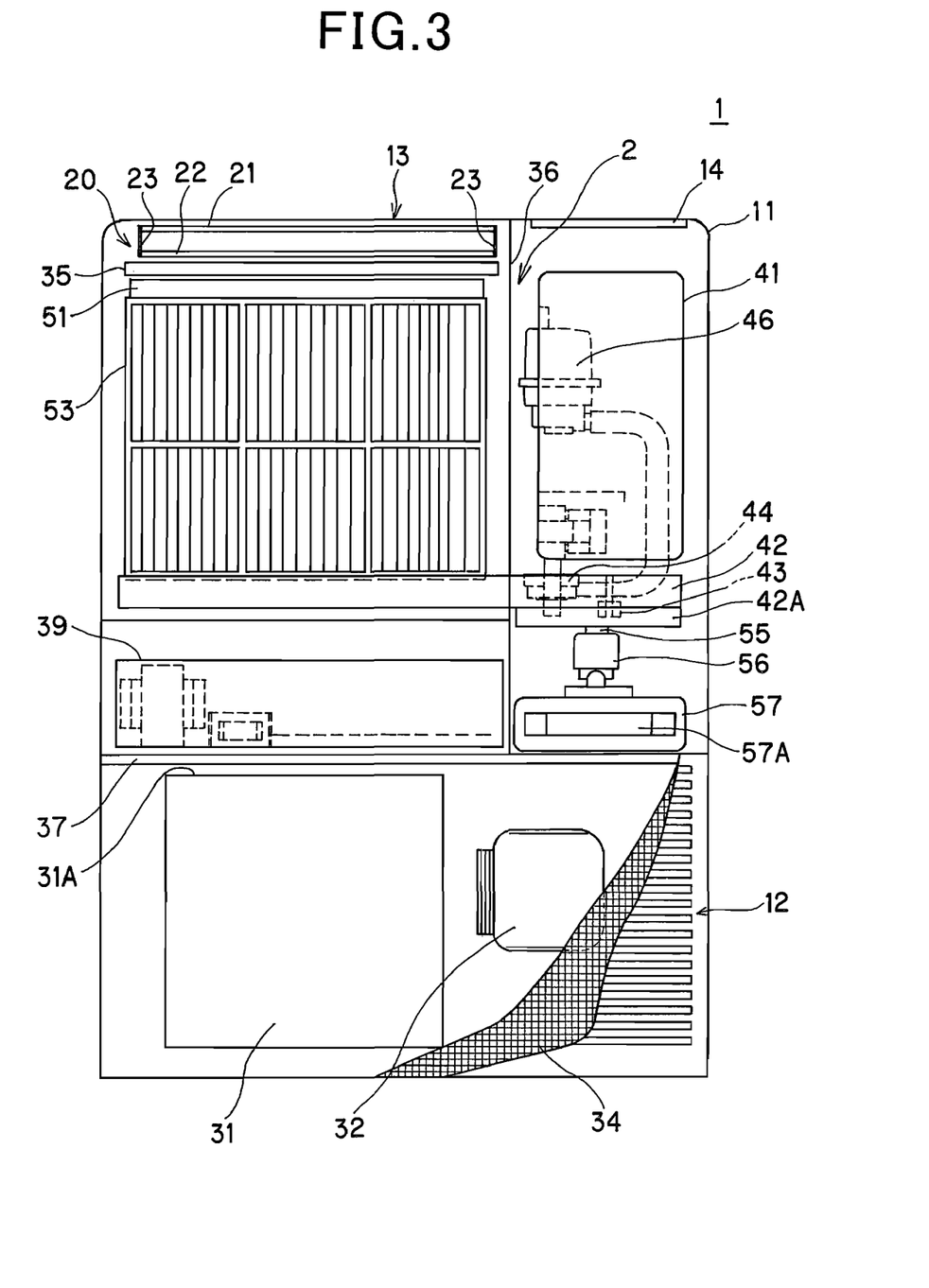
FIG. 3 is a partially fracture front view showing the internal construction of the air filtering apparatus.
Figure 4:
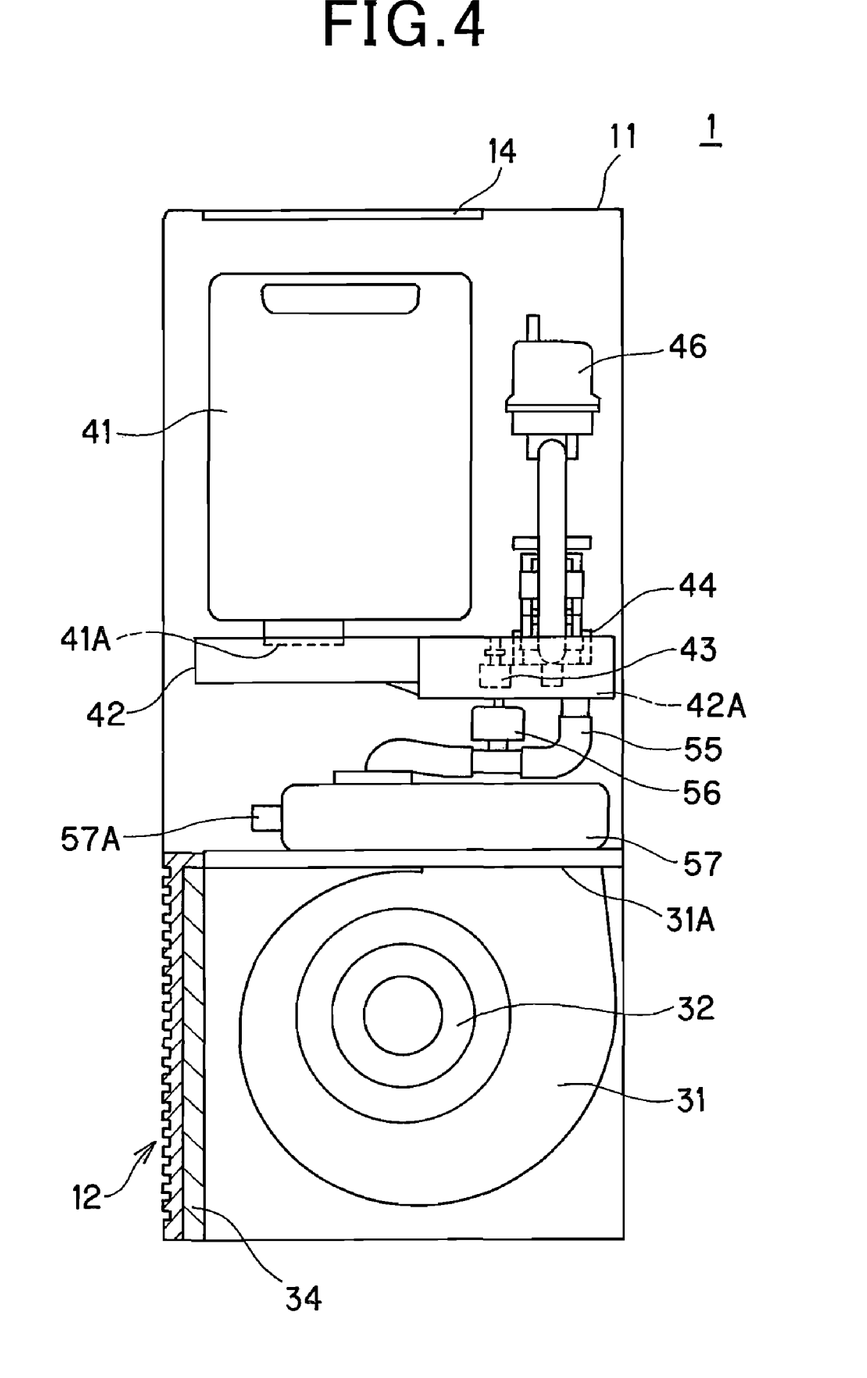
FIG. 4 is a left-side sectional view showing the internal construction of the air filtering apparatus.
Figure 5:
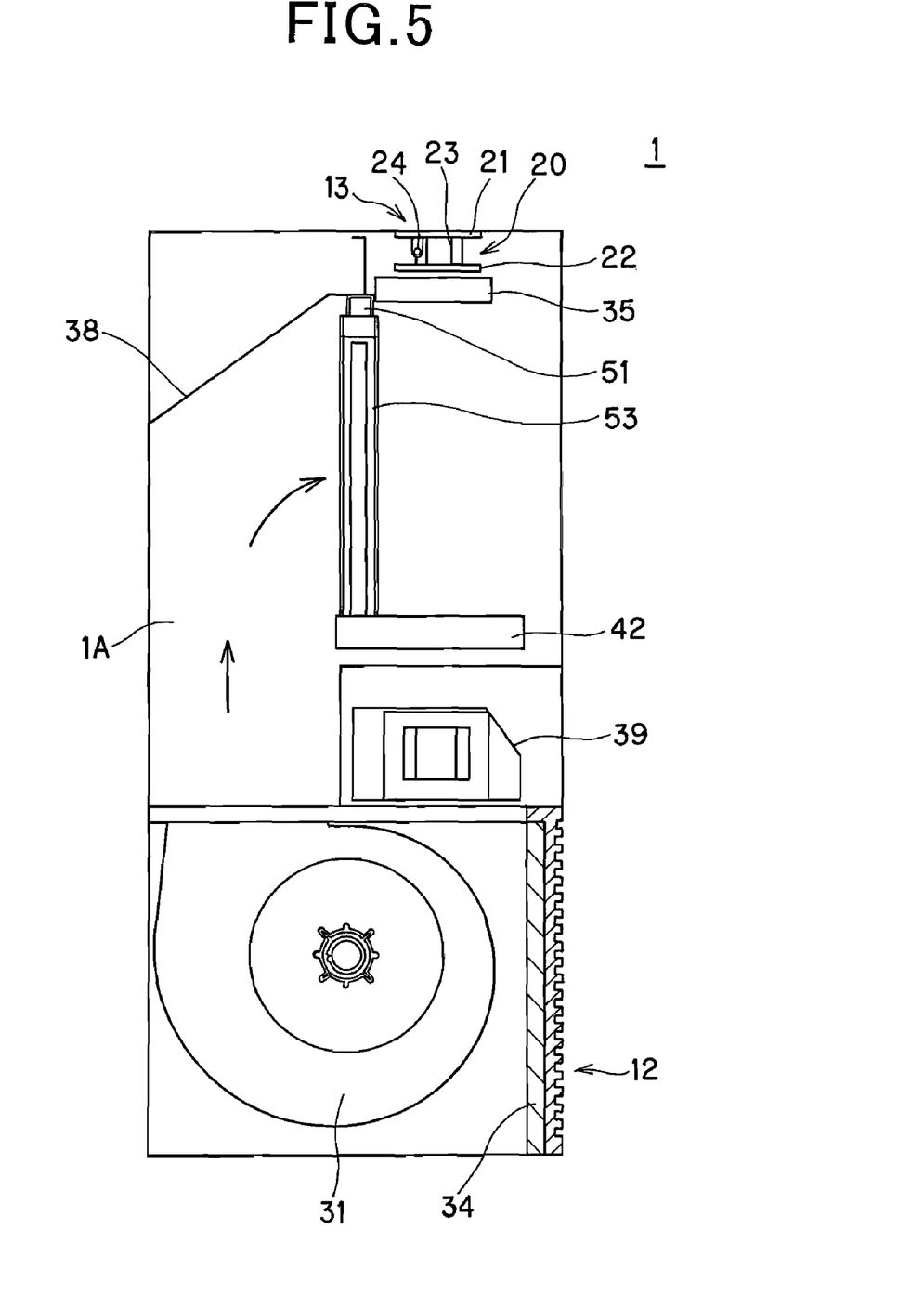
FIG. 5 is a right-side sectional view showing the internal construction of the air filtering apparatus.
Figure 6:
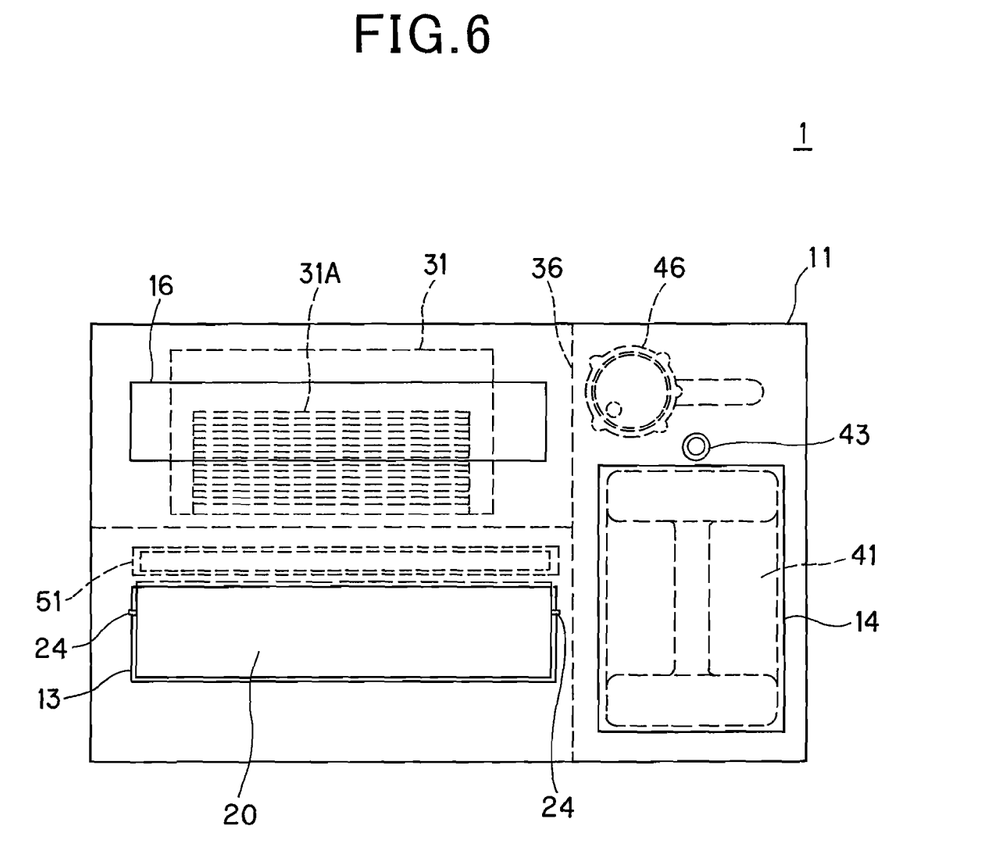
FIG. 6 is a top view showing the internal construction of the air filtering apparatus.

FIG. 3 is a partially fracture front view showing the construction of the air filtering apparatus 1, FIG. 4 is a left-side sectional view, FIG. 5 is a right-side sectional view and FIG. 6 is a top view.

The inside of the housing 11 is partitioned vertically into upper and lower chambers by a support plate 37. An air blowing fan 31 and a fan motor 32 are accommodated in the lower chamber. The air blowing fan 31 is driven by the fan motor 32 to suck indoor air through the suction grille 12 and blow out the air from the air flow-out port 31A. The air flow-out port 31A of the air blowing fan 31 is at the back side portion of the housing 11 so as to be placed face up, and an opening is formed in the support plate 37 so as to be overlapped with the air flow-out port 31A. The opening of the support plate 37 intercommunicates with the space 1A extending vertically at the back side of the housing 11. An air guide plate 38 which is tilted to the front side of the housing 11 is disposed at the upper portion of the space 1a as shown in FIG. 5, and the front end of the air guide plate 38 is brought into contact with the upper end of a water spray box 51 described later.

Therefore, air blown out from the air flow-out port 31A of the air blowing fan 31 passes through the space 1A as indicated by an arrow X in FIG. 5, and blows to the back side of a gas-liquid contact member 53 described later.

Furthermore, a pre-filter 34 is disposed in the housing 11 so as to be overlaid on the back side of the suction grille 12. The pre-filter 34 is a filter for collecting materials (foreign materials such as dust, grass pollen, etc.) of 10 μm or more in particle diameter, for examples. Foreign materials such as dust, grass pollen, etc. are removed by the pre-filter 34, and air from which these foreign materials are removed is sucked by the air blowing fan 31.

An electrical component box 39 and an electrolytic water circulating unit 2 are disposed on the support plate 37. In the electrical component box 39 are accommodated various kinds of electrical components such as a control board on which various kinds of devices constituting a controller 60 described later are mounted, etc.

The electrolytic water circulating unit 2 comprises a water receiving tray 42, a water receiving tray float switch 43, a circulating pump 44, an electrolytic bath 46, a water spray box 51 and the gas-liquid contact member 53. The water receiving tray 42 is located above the electrical component box 39, and receives water dropped form the gas-liquid contact member 53. Accordingly, the water receiving tray 42 has a depth to stock a predetermined amount of water. One end portion of the water receiving tray 42 is designed to have a bottom deeper than the other portion, and it serves as a stock portion 42A. The water receiving tray float switch 43 for detecting the water level is disposed at the stock portion 42A. The water receiving tray float switch 43 is turned on when the water level of the stock portion 42A is lower than a predetermined water level.

The water supply tank 41 is disposed above the stock portion 42A, and it is designed so as to supply water from the water supply tank 41 to the stock portion 42A. In detail, a float valve (not shown) is provided to a water supply port 41A formed at the lower end of the water supply tank 41. When the water level of the stock portion 42A is lower than the water supply port 41A, a required amount of water is supplied form the water supply tank 41 so that the water level of the stock portion 42A is kept constant.

Furthermore, a circulating pump 44 is disposed between the water supply tank 41 and the housing 11 in the upper space of the stock portion 42A. The circulating pump 44 operates according to the control of a controller 60 described later to pump up water stocked in the stock portion 42A and feed the water to an electrolytic bath 46. The electrolytic bath 46 contains plural electrodes described later therein, and a voltage is applied to these electrodes from the controller 60 to electrolyze water and thus generate electrolytic water. The electrolytic water generated in the electrolytic bath 46 is pushed out from the electrolytic bath 46 by water discharged by the circulating pump 44, and supplied to a water spray box 51.

The water spray box 51 is a tubular member assembled to the upper portion of the gas-liquid contact member 53. Plural water spray holes (not shown) are formed at the lower surface of the water spray box 51, and electrolytic water is dropped form the water spray holes to the gas-liquid contact member 53. The gas-liquid contact member 53 is a substantially planar member infiltrated with electrolytic water dropped from the water spray box 51, and it is disposed above the water receiving tray 52 together with the water spray box 51. As shown in detail in FIG. 5, the gas-liquid contact member 53 is substantially vertically erected, and the lower end thereof intrudes into the water receiving tray 42. Furthermore, the water spray box 51 assembled to the upper portion of the gas-liquid contact member 53 is brought into contact with the tip of the air guide plate 38. Therefore, the air passed through the space 1A by the air blowing fan 31 is guided to the gas-liquid contact member 53 side by the air guide plate 38, and passes through the gas-liquid contact member 53.

The gas-liquid contact member 53 is a filter member having a honeycomb structure. In details, the gas-liquid contact member 53 has the structure that an element portion which is brought into contact with gas is supported by a frame. The element portion is constructed by laminating corrugated-plate type corrugated members and flat-plate type planar members, and many openings having substantially triangular shapes are formed among these corrugated members and the planar members. Accordingly, the gas-liquid contact member 532 has the structure in which a large gas contact area can be secured when gas is passed through the element portion, electrolytic water can be dropped and also clogging occurs hardly.

Furthermore, a water distributing sheet (not shown) is provided to the gas-liquid contact member 53 in order to efficiently disperse electrolytic water dropped from the water spray box 51 into the element portion. The water distributing sheet is a sheet (woven fabric, non-woven cloth or the like) formed of textile material having liquid permeability, and one or plural water distributing sheets are provided along the cross-section taken along the thickness direction of the gas-liquid contact member 53.

Furthermore, the gas-liquid contact member 53 and the water supply tank 41 are insulated from each other by a partition plate 36. The partition plate 36 blocks off the space 1A and the side of the gas-liquid contact member 53, and makes air smoothly pass through the gas-contact member 53.

Here, the respective parts of the gas-liquid contact member 53 (containing the frame, the element portion and the water distributing sheet) are formed of materials which are little deteriorated by electrolytic water, such as polyolefin-based resin (polyethylene resin, polypropylene resin or the like), PET (polyethylene terephthalate) resin, vinyl chloride resin, fluorocarbon resin (PTFE, PFA, ETFE or the like), ceramic material or the like. In this embodiment, PET resin is assumed to be used.

Furthermore, the respective parts of the gas-liquid contact member 53 is subjected to a hydrophilic treatment to enhance the affinity to electrolytic water. Accordingly, water retentivity (wettability) of electrolytic water of the gas-liquid contact member 53 is kept, and the contact between active oxygen species (active oxygen materials) described later and indoor air can be kept for a long time. Furthermore, electrolytic water having a mildewproof action is dropped to the gas-liquid contact member 53, so that breeding of fungus, etc. can be avoided without taking any mildewproof action to the gas-liquid contact member 53.

Air passing through the gas-liquid contact member 53 is exhausted through an air blow-out filter 35 disposed below the air blow-out port 13. The air blow-out filter 35 is a filter for preventing invasion of foreign materials from the air blow-out port 13 into the housing 11. The air blow-out port filter 35 has a net, woven fabric, non-woven cloth or the like (not shown), and these materials are formed of synthetic resin, and preferably formed of the material constituting the gas-liquid contact member 53. The air blow-out filter 35 is preferably of moderately loose texture so that the air flowing resistance of air passing through the gas-liquid contact member 53 is not remarkably increased.

As described above, the louver 20 is disposed at the air blow-out port 13, and it is constructed by an upper plate 21 having a size at which the air blow-out port 13 can be closed, a lower plate 22 disposed in parallel to the upper plate 21 at the lower side of the upper plate 21, and joint portions 23 for joining the upper plate 21 and the lower plate 22. The joint portions 23 are plate-shaped members provided to the right and left end portions of each of the upper plate 21 and the lower plate 22, and a pin 24 is erected from each of the joint portions 23. These two pins 24 are projected from both the side ends of the louver 20 to the housing 11 side, and fitted to receivers (not shown) provided at the sides of the air blow-out port 13 to support the louver 20. The two pins 24 are freely rotatably supported at the receivers, and joined to a louver driving motor 68 as a driving unit (see FIG. 8). The pins 24 are driven by the louver driving motor 68 and the louver 20 is turned in connection with the driving of the pins 24.

Under the state that the louver 20 is substantially in parallel to the upper face of the housing 11, the air blow-out port 13 is substantially closed by the upper plate 21. This state will be referred as "close state" of the louver 20. On the other hand, the state that the louver 20 is tilted with respected to the upper face of the housing 11 will be referred to as "open state".

Under the open state of the louver 20, air passing through the gas-liquid contact member 53 can be discharged from the air blow-out port 13. Here, the louver 20 is adjusted to any tilt angle position by the louver driving motor 68, and held at the title angle position. Therefore, the air blowing direction from the air-blow port 13 can be adjusted by the louver 20. Furthermore, the louver 20 has a two-vane structure in which the upper plate 21 and the lower plate 22 are arranged in parallel to each other so as to be spaced from each other at a predetermined interval, so that the louver 20 has an action of rectifying the air blown out from the air blow-out port 13. Accordingly, there is an advantage that air can be smoothly discharged in conformity to the tilt angle of the louver 20.

Furthermore, if the louver 20 is set to the close state while the fan motor 32 is stopped, air in the housing 1 hardly leaks to the outside. Therefore, as described later, when active oxygen species of high concentration are generated in the electrolytic bath 46, odor inherent to these materials hardly leak to the outside. Accordingly, the active oxygen species of high concentration can be utilized with keeping comfortable the indoor environment under which the air filtering apparatus 1 is set.

Figure 7A:
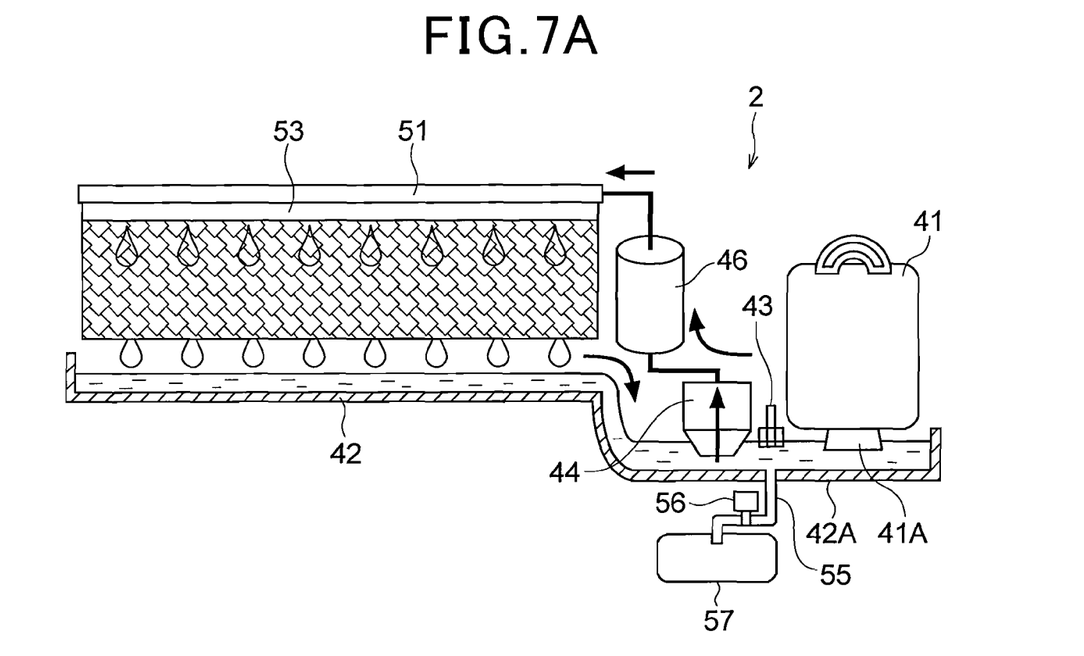
FIG. 7A is a diagram showing the construction of an electrolytic water circulating unit.
Figure 7B:
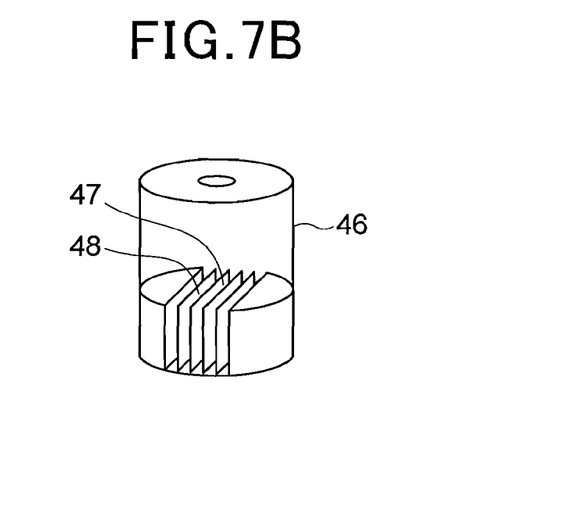
FIG. 7B is a diagram showing the construction of an electrolytic bath.

FIGS. 7A and 7B are diagrams showing the aspect of supplying electrolytic water, wherein FIG. 7A is a diagram showing the construction of the electrolytic water circulating unit 2, and FIG. 7B is a diagram showing the detailed construction of the electrolytic bath 46.

When the water supply tank 41 filled with tap water is set in the air filtering apparatus 1, the tap water is supplied form the water supply tank 41 to the water receiving tray 42 as described above, and the water level of the water receiving tray 42 reaches a predetermined level. Water in the water receiving tray 42 is pumped by the circulating pump 44, and supplied to the electrolytic bath 46. As shown in FIG. 7B, the electrolytic bath 46 is equipped with at least one pair of positive and negative electrodes 47 and 48, and by applying a voltage between the electrodes 47 and 48, tap water supplied to the electrolytic bath 46 is electrolyzed and electrolytic water containing active oxygen species is generated. Here, the active oxygen species is oxygen having higher oxidizing activity than normal oxygen and relevant materials thereto, and contain not only so-called narrowly-defined active oxygen such as superoxide anion, singlet oxygen, hydroxyl radical and hydrogen peroxide, but also so-called broadly-defined active oxygen such as ozone, hypochlorous acid, hypohalous acid, etc. The electrolytic bath 46 is disposed in proximity to the gas-liquid contact member 53, and thus the active oxygen species generated by electrolyzing tap water can be immediately supplied to the gas-liquid contact member 53.

The electrodes 47, 48 are constructed by two electrode plates each of which comprises a base of Ti (titan) and a coated layer of Ir (iridium), Pt (platinum).

More specifically, by supplying current to tap water through the electrodes 47, 48, hydrogen ion (H$^+$) and hydroxide ion in water react with each other according to the following reaction formula (1) at the cathode:

$$4H^+ + 4e^- + (4OH^-) \rightarrow 2H_2 + (4OH^-) \tag{1}$$

Furthermore, water is electrolyzed according to the following reaction formula (2) at the anode:

$$2H_2O \rightarrow 4H^+ + O_2 + 4e^- \tag{2}$$

At the same time, chlorine ion (Cl$^-$) contained water reacts according to the following reaction formula (3), and chlorine (Cl$_2$) is generated:

$$2Cl^- \rightarrow Cl_2 + 2e^- \tag{3}$$

Furthermore, Cl$_2$ thus generated reacts with water and hypochlorous acid (HClO) and hydrogen chloride (HCl) is generated:

$$Cl_2 + H_2O \rightarrow HClO + HCl \tag{4}$$

Hypochlorous acid occurring at the anode is contained in the broadly-defined active oxygen species and has strong oxidizing action and a bleaching action. Water solution in which hypochlorous acid is dissolved, that is, electrolytic water generated in the air filtering apparatus 1 exercises various kinds of air cleaning effects such as inactivation of virus, etc., sterilization, decomposition of organic compounds, etc. When electrolytic water containing hypochlorous acid is dropped from the water spray box 51 to the gas-liquid contact member 53, air blown out from the air blowing fan 31 is brought into contact with hypochlorous acid in the gas-liquid contact member 53. Accordingly, virus, etc. floating in the air are inactivated, and also odor materials contained in the air concerned react with hypochlorous acid to be decomposed or ionized, so that the order materials are dissolved in the water. Accordingly, air filtering and deodorization are performed, and cleaned air is discharged from the gas-liquid contact member 53.

An inactivating mechanism of virus, etc. by the active oxygen species will be described by exemplifying influenza virus. The active oxygen species functions to break down and vanish (remove) the surface protein (spike) of the virus concerned which is indispensable for infection. When the surface protein of influenza virus is broken down, the influenza virus is not joined to a receptor which is necessary for infection of the virus concerned, so that infection can be prevented. Therefore, influenza virus floating in the air is brought into contact with the electrolytic water containing the active oxygen species in the gas-liquid contact member 53, so that the influenza virus loses so-called infection power, and thus the infection can be prevented.

In the air filtering apparatus 1 of this embodiment, water stocked in the water receiving tray 42 can be properly discharged. Specifically, as shown in FIGS. 2 to 7, a tank-like drain receiver 57 which has a predetermined width and is equipped with an opening at the upper portion thereof is disposed below the water stock portion 42A. The drain receiver 57 is mounted on the support plate 37 (FIG. 2), and it can be inserted and taken out into/from the drain receiver take-out port 15 of the housing 11 (FIG. 1). The drain pipe 55 is joined to the stock portion 42A of the water receiving tray 42, and a drain valve 56 for opening/closing the drain pipe 55 is provided to the drain pipe 55. The tip of the drain pipe 55 extends downwardly, and intrudes from the opening of the drain receiver 57 into the opening portion provided in the upper surface of the drain receiver 57.

The bottom surface of the stock portion 42A is opened at the joint portion to the drain pipe 55 so that water in the stock portion 42A flows out from the open portion. Therefore, the drain valve 56 is opened under the control of the controller 60 (FIG. 8), and the water in the water receiving tray 42 passes through the drain pipe 55 and flows to the drain receiver 57. As described above, the drain pipe 55 branched from the electrolytic water circulating unit 2 is used, and the opening/closing of the drain valve 56 is controlled, whereby water in the electrolytic water circulating unit 2 can be withdrawn/discharged by the drain receiver 57. Furthermore, the drain receiver 57 is provided with a grip portion 57A which can be easily grasped, and thus it can be easily inserted and taken out into/from the drain receiver take-out port 15 (FIG. 1).

Figure 8:
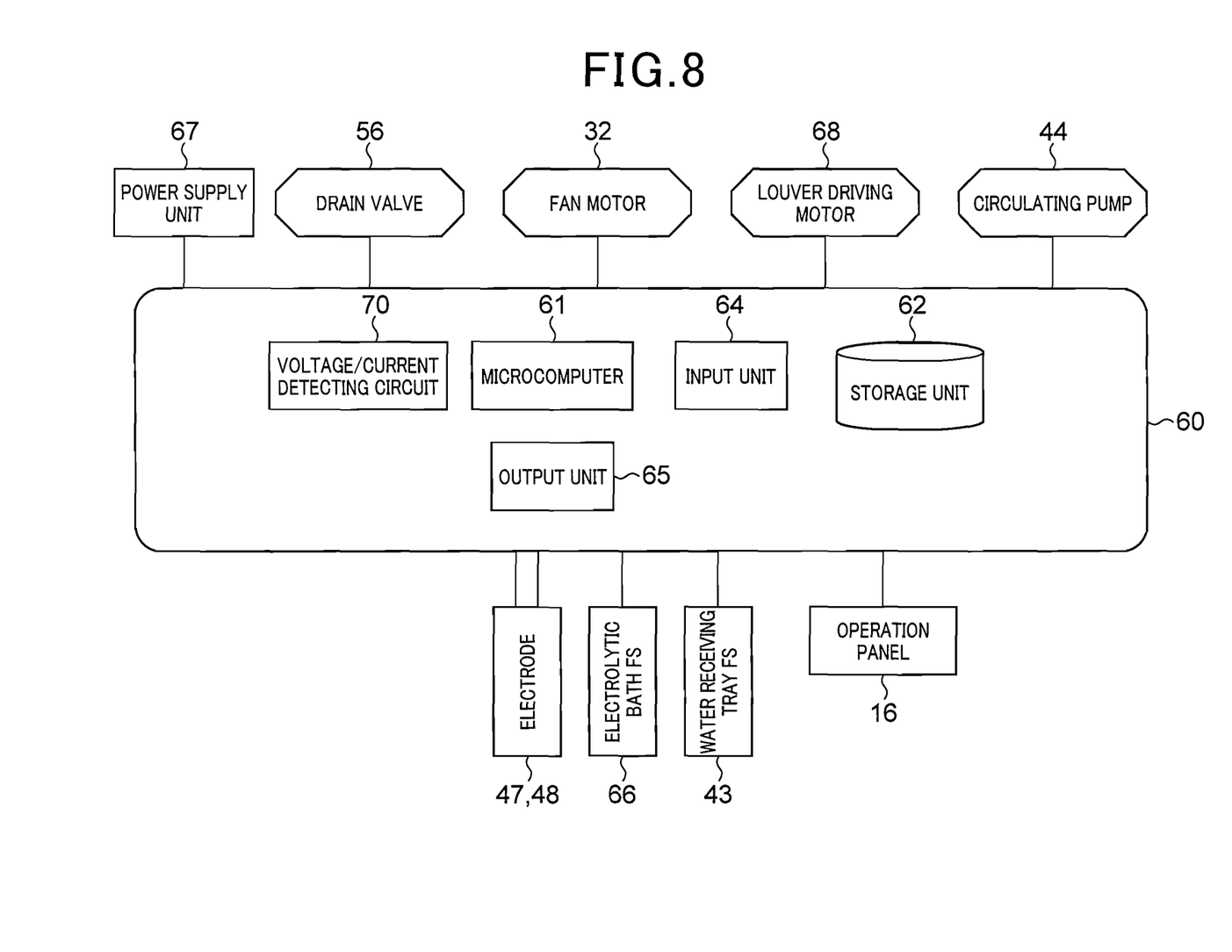
FIG. 8 is a functional block diagram showing the construction of a control system for the air filtering apparatus.

FIG. 8 is a functional block diagram showing the construction of the control system of the air filtering apparatus 1.

As shown in FIG. 8, in the air filtering apparatus 1, the fan motor 32, the circulating pump 44, the drain valve 56, the louver driving motor 68 for opening/closing the louver 20 and the power supply portion 67 for supplying power to the respective parts are connected to the controller 60, and operated according to the control of the controller 60.

Furthermore, various kinds of switches, indicator lamps, etc. disposed on the operation panel 16 are connected to the controller 60, and also the water receiving tray float switch 43, the electrodes 47, 48, and the electrolytic bath float switch 66 for detecting the water level in the electrolytic bath 46 are connected to the controller 60.

The controller 60 comprises various kinds of electrical parts mounted on a control board accommodated in an electrical component box 39, and specifically it includes a microcomputer 61 for controlling the whole of the air filtering apparatus 1, a storage unit 62 for storing control programs executed by the microcomputer 61 and data such as control parameters, etc., an input unit 64 for detecting an operation of the operation panel 16 and outputting the operation content to the microcomputer 61, an output unit 65 for outputting the processing result of the microcomputer 61 by controlling turn-on of the indicator lamps (not shown) of the operation panel 16 or the like, and a voltage/current detecting circuit 70 described later.

The microcomputer 61 reads a control program stored in the storage unit 62 and executes the control program to control the overall air filtering apparatus 1. Specifically, when the operation of instructing start of the operation is carried out on the operation panel 16 and the information representing this operation is input from the input unit 64, the microcomputer 61 operates the circulating pump 44 to start the circulation of water, and also applies power from a power supply unit 67 between the electrodes 47, 48 to make current flow between the electrodes 47 and 48, thereby performing an electrolyzing operation of generating electrolytic water. Thereafter, the microcomputer 61 starts the operation of the fan motor 32 to start air blowing of the air blowing fan 31. Through the above series of operations, the air filtering operation of the air filtering apparatus 1 is started. In connection with the start of the air filtering operation, the microcomputer 61 controls the output unit 65 to indicate that the air filtering apparatus is under operation, and also drives the louver driving motor 68 according to the operation on the operation panel 16, thereby adjusting the title angle of the louver 20.

Figure 9:
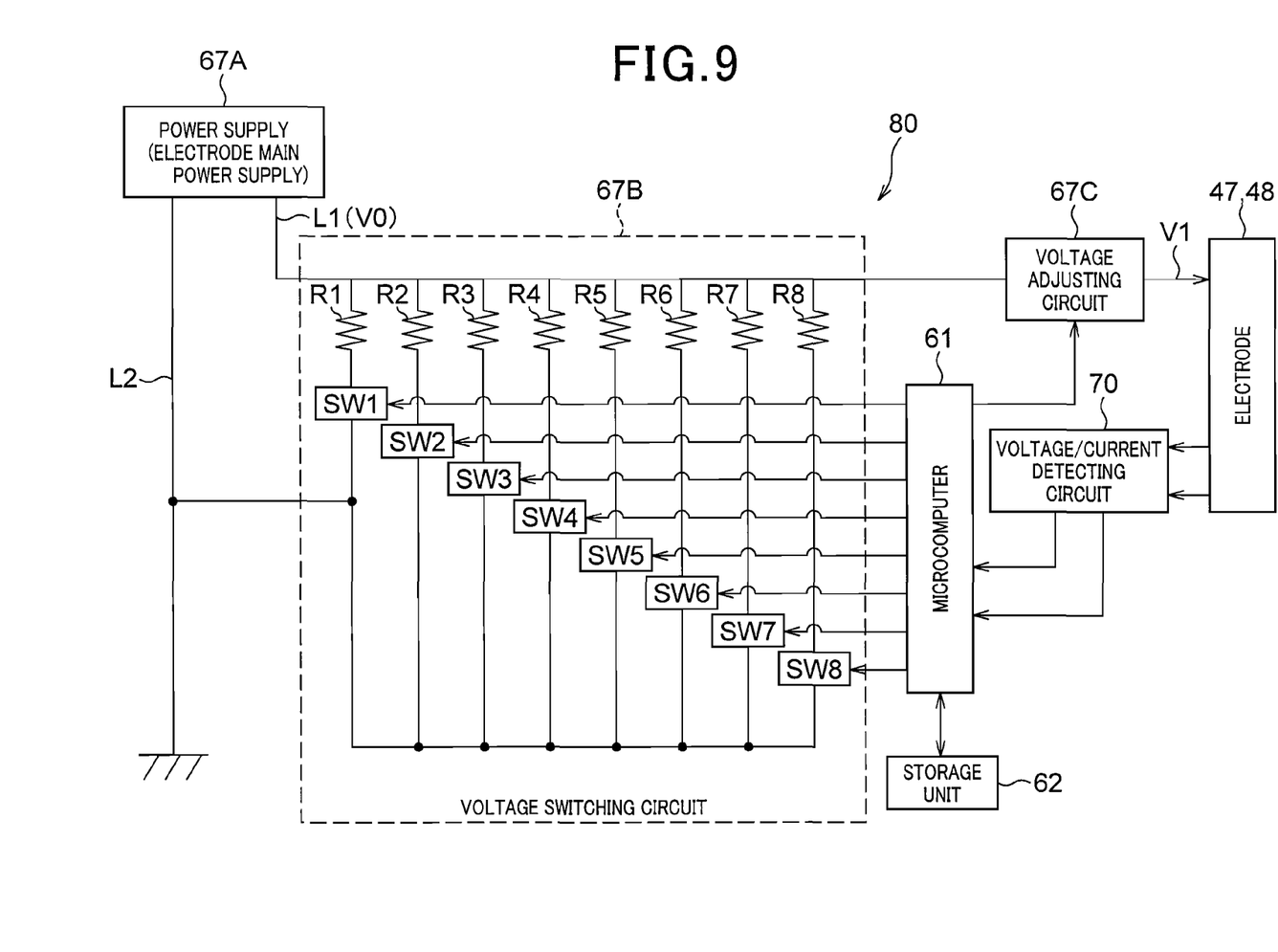
FIG. 9 is a diagram showing a circuit construction for electrolyzing operation.

FIG. 9 is a circuit diagram showing the electrolyzing operation.

In this embodiment, the power supply unit 67 includes a power supply (electrode main power supply) 67A for electrolyzing operation, a voltage switching circuit 67B for switching the voltage from the power supply 67A, and a voltage adjusting circuit 67C for adjusting the power supply voltage switched by the voltage switching circuit 67B and applying the adjusted power supply voltage between the electrodes 47, 48. These units are operated according to the control of the microcomputer 61, and these units constitute a voltage variable circuit 80 for varying the power supply voltage applied between the electrodes 47 and 48.

As shown in FIG. 9, the voltage switching circuit 67B includes plural resistance elements Rk (k=1 to n: n=8 in this embodiment) which function as voltage switching resistors and are different in resistance value, and plural switching elements SWk (k=1 to n: n=8 in this embodiment) for selectively connecting the resistance element Rk between a power supply line L1 of the power supply 67A and a ground line L2.

ON/OFF operation of each switching element SWk is controlled by the microcomputer 61. Specifically, any one switching element SWk is selectively subjected to ON-control by the microcomputer 61, whereby one resistance element Rk is connected (parallel-connected) to the power supply 67A, and the voltage based on the resistance element Rk is supplied as an output voltage V0 to the voltage adjusting circuit 67C.

In this embodiment, the resistance element Rk is switched so that the resistance element R1 is adjusted to a resistance value at which the output voltage V0 is set to 3.5V, the resistance element R2 is set to a resistance value at which the output voltage V0 is set to 7.0V, the resistance element R3 is adjusted to a resistance value at which the output voltage V0 is set to 10.5V, etc., whereby the output voltage V0 can be switched every constant potential difference $\Delta V$ (3.5V).

The voltage adjusting circuit 67C adjusts the output voltage V0 by pulse width modulation (PWM) to achieve an output voltage (power supply voltage) V1. Under the control of the microcomputer 61, the voltage adjusting circuit 67C adjusts the output voltage V0 of the voltage switching circuit 67B represented by a solid line in FIG. 10 within the potential difference $\Delta V$ which is switchable by the voltage switching circuit 67B, thereby achieving a broad output voltage characteristic (output voltage V1) of 20[V] or more covering even intermediate voltage values which are not covered by the output voltage V0 of the voltage switching circuit 67B as indicated by a wiggle line.

Figure 10:
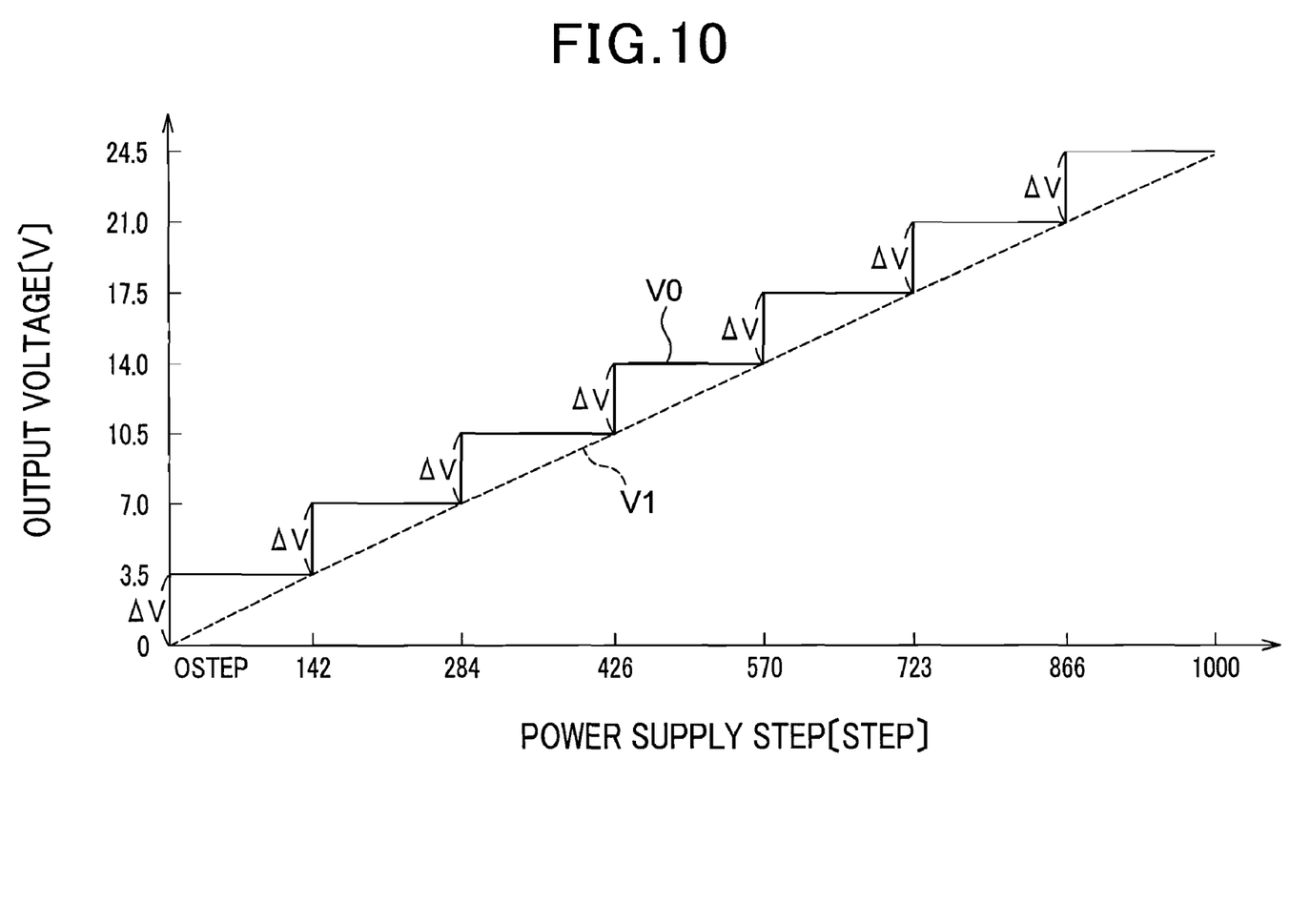
FIG. 10 is a diagram showing an output voltage characteristic of a voltage switching circuit and a voltage adjusting circuit.

In other words, according to this embodiment, the voltage switching circuit 67B is controlled by the microcomputer 61 so as to selectively output the output voltage V0 nearest to the output voltage V1 after the adjustment of the voltage adjusting circuit 67C within the adjustable range of the voltage adjusting circuit 67C. Accordingly, the maximum voltage drop in the voltage adjusting circuit 67C can be suppressed to the potential difference $\Delta V$ (3.5V) although the broad output voltage characteristic of 20[V] or more can be achieved.

The abscissa axis of FIG. 10 represents a power supply step used as a control value for indicating the output voltage V1. The power supply step 0 [STEP] represents the output voltage V1=0, the power supply step 142 [STEP] represents the output voltage V1=3.5[V], . . . , and the power supply step 1000 [STEP] represents the output voltage V1=24.5[V].

As shown in FIG. 9, the voltage/current detecting circuit 70 detects the voltage value and the current value between the electrodes 47, 48 to detect the electrical conductivity of water in the air filtering apparatus 1. Specifically, the voltage/current detecting circuit 70 operates according to the control of the microcomputer 61, and it is intermittently or continuously driven during the electrolyzing operation to output the detection result to the microcomputer 61, whereby the microcomputer 61 determines the electrical conductivity of water corresponding to the reciprocal number of the voltage value/current value (that is, the resistance value) by calculation.

Furthermore, in the storage unit 62 is stored target current setting information for setting target current It to flow between the electrodes 47 and 48 on the basis of the electrical conductivity of water which varies in accordance with the type of water (for example, tap water or the like), electrolysis, pollution of water, etc. Specifically, table data for associating the electrical conductivity of water with target current It to set the concentration of electrolytic water (hypochlorous acid) to a target concentration is applied as the target current setting information, and the microcomputer 61 can accurately specify the target current It on the basis of the electrical conductivity of water achieved from the detection result of the voltage/current detecting circuit 70 by referring to the table data.

Next, the control under the electrolysis operation will be described.

Figure 11:
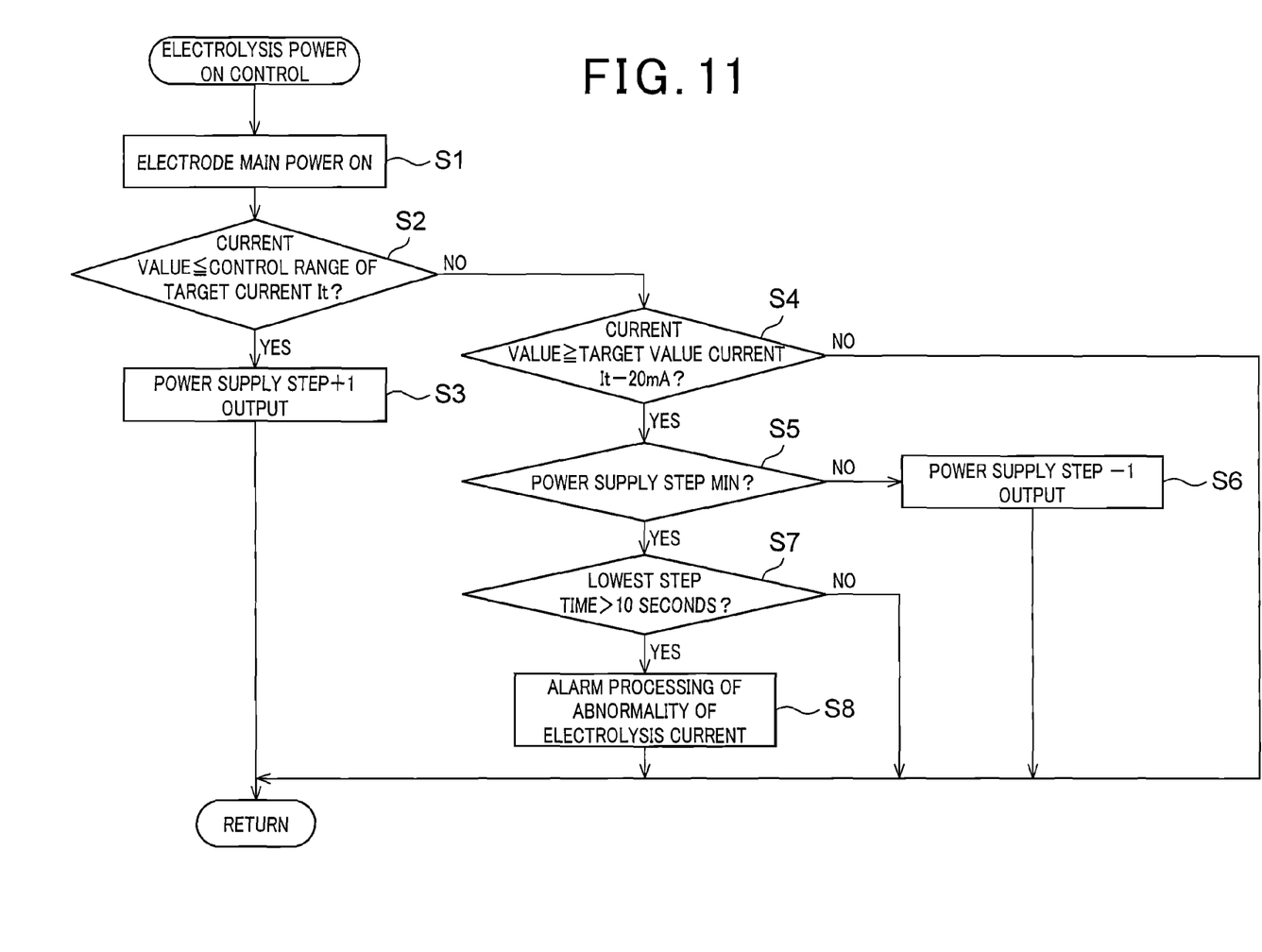
FIG. 11 is a flowchart showing the power supply control under electrolyzing operation.

FIG. 11 is a flowchart showing the power supply control (ON control of electrolyzing power supply) during electrolyzing operation. Before the electrolyzing operation, the power supply (electrode main power supply) 67A is turned off, and only the switching element SW1 (the switching element for setting the output voltage V0 to the lowest voltage (3.5V)) out of the switching elements SWk of the voltage switching circuit 67B is set to ON for the purpose of protecting the circuit while all the remaining switching elements SWk are set to OFF.

When the electrolyzing operation is started, the microcomputer 61 first set to the power supply (electrode main power supply) 67A to ON (step S1) and supplies power of the power supply between the electrodes 47, 48. Subsequently, the microcomputer 61 achieves the detection result of the voltage/current detecting circuit 70 to detect the electrical conductivity of water, specifies the target current It on the basis of the target current setting information (for example, the table data) stored in the storage unit 62 and compares the current value detected by the voltage/current detecting circuit 70 with the target current It (step S2). This comparison processing is performed by judging through the microcomputer 61 whether the detected current value is not more than a control range based on the target current It (for example, in the range of ±20 [mA] from the target current It.

In the processing of this step 2, if the detected current value is not more than the control range based on the target current It (step S2: YES), the microcomputer 61 adds the power supply step with "1" (step S3), and returns the processing to the step S1. Accordingly, the power supply step is incremented every "1" at a predetermined period (for example, 10 ms) insofar as the detected current value is not more than the control range based on the target current It. Therefore, the power supply voltage (output voltage V1) applied between the electrodes 47, 48 is gradually increased from 0V so as to be along the output voltage characteristic (output voltage V1) indicated by the wiggle line of FIG. 10 so that the output voltage V1 of the voltage adjusting circuit 67C is first gradually increased from 0 to 3.5[V] under the state that the output voltage V0 of the voltage switching circuit 67B is equal to 3.5[V], and then the output voltage V0 of the voltage switching circuit 67B is switched to 7.0[V], whereby the output voltage V1 of the voltage adjusting circuit 67C is gradually increased from 3.5[V] to 7.0[V].

When the power supply voltage (output voltage V1) applied between the electrodes 47, 48 is increased and the detected current value reaches the control range based on the target current It (step S2, NO) as described above, the microcomputer 61 temporarily judges whether the detected current value is an abnormal current value or not (step S4). If the detected current value is not the abnormal current value (step S4: NO), the power supply step is fixed and held to the voltage (output voltage V1) at that time point. Accordingly, the current value flowing between the electrodes 47, 48 is subjected to feed-back control so that it is within the control range based on the target current It.

The temporary judgment as to whether the detected current value is an abnormal current value or not (step S4) is specifically performed by judging whether the detected current value exceeds the target current It and also whether the difference between the current value and the target current It is equal to a predetermined value or more. In this embodiment, when the microcomputer 61 judges that the detected current value is not more than (the target current It−20 [mA]), the detected current value is temporarily judged as an abnormal current value.

In this case, the microcomputer 61 judges whether the power supply step is equal to the minimum value MIN (0 [STEP]) or not (step S5). If it is not the minimum value MIN (step S5: NO)< the microcomputer 61 subtracts only "1" from the power supply step (step S6), and returns the processing to the step S1. Accordingly, every "1" is subtracted from the power supply step (i.e., the power supply step is decremented one by one) at a predetermined period (for example, 10 ms) insofar as the detected current value is temporarily judged as the abnormal current value. Accordingly, if the voltage varying circuit 80 is normal, the power supply voltage (output voltage V1) is gradually reduced so as to be along the output voltage characteristic (the output voltage V1) represented by the wiggle line of FIG. 10, and the current value flowing between the electrodes 47 and 48 is subjected to feed-back control so as to be within the control range based on the target current It.

On the other hand, if the detected current is continued to be temporarily judged as an abnormal current value although the power supply step is decremented one by one at the predetermined period (for example, 10 ms), the microcomputer 61 stands ready (step S7) until a predetermined standby time (for example, 10 seconds) elapses when the power supply step reaches the minimum value MIN (step S5: YES). If the detected current is temporarily judged as an abnormal current value even after the standby time elapses (step S7: YES), alarm processing of reporting that the electrolysis current value is abnormal is executed (step S8).

For example, the processing of turning on an alarm lamp (not shown) of the operation panel 16 or the processing of emitting alarm sound by driving a buzzer (not shown) is applied as the alarm processing. The above processing is the control under electrolyzing operation.

As described above, according to this embodiment, the voltage varying circuit 80 for varying the power supply voltage applied between the electrodes 47, 48 is equipped with the voltage switching circuit 67B for switching the power supply voltage, and the voltage adjusting circuit 67C for adjusting the output voltage V0 of the voltage switching circuit 67B and applying the adjusted output voltage V1 between the electrodes 47, 48, and the voltage switching circuit 67B is controlled to switch and output the output voltage V0 nearest to the output voltage V1 adjusted by the voltage adjusting circuit 67C. Therefore, the voltage drop of the power supply by the voltage adjusting circuit 67C can be suppressed to the potential difference ΔV (3.5V) which the voltage switching circuit 67B can increase or reduce at maximum.

Accordingly, as compared with a power supply varying circuit which achieves the same broad output voltage characteristic of 20[V] or more as this embodiment by using only the voltage adjusting circuit for adjusting the voltage by pulse width modulation or the like, a radiating device such as a heat sink or the like which radiates heat of the power supply circuit containing the power supply unit 67 and the voltage varying circuit 80 can be more remarkably miniaturized, so that the large-scale design of the power supply unit 67 can be avoided, and also power consumption caused by thermal loss can be reduced.

Furthermore, in this embodiment, the voltage switching circuit 67B is constructed by the plural resistance elements Rk which function as voltage switching resistors and are different in resistance value, and the plural switching elements SWk. Therefore, the circuit construction is simple, and thus the large-scale design of the power supply unit 67 can be avoided.

Still furthermore, according to this embodiment, the electrical conductivity of water is detected, the target current It is set, and the output voltage V1 applied between the electrodes 47, 48 is subjected to the feedback control so that the current value between the electrodes 47, 48 is within the control range based on the target current It. Therefore, the concentration of electrolytic water (active oxygen species such as hypochlorous acid or the like) can be stabilized even when the type of water (tap water or the like) is different or the ion concentration is varied due to electrolysis, pollution of water or the like.

In addition, when the current value between the electrodes 47 and 48 is out of the control range based on the target current It, the output voltage V1 applied between the electrodes 47 and 48 is controlled to be gradually varied, and when the current value between the electrodes 47 and 48 reaches the control range based on the target current It, the output voltage V1 is fixed to the output voltage V1 at that time point. Therefore, the current value between the electrodes 47 and 48 can be surely controlled to be within the control range concerned.

Still furthermore, according to this embodiment, when there is satisfied the condition that the current value between the electrodes 47 and 48 exceeds the target current It and the difference between the current value and the target current It is equal to the predetermined value or more, the output voltage V1 applied between the electrodes 47 and 48 is gradually reduced to the lowest voltage, and if the above condition is satisfied even after the output voltage V1 is set to the lowest voltage, the alarm processing is executed. Therefore, the abnormality of the air filtering apparatus 1 can be detected with high precision and reported with protecting the circuit.

The air filtering apparatus 1 according to this embodiment is an example, and various modifications may be properly made without departing from the subject matter of the present invention. For example, in the above embodiment, the voltage switching circuit 67B selectively connects any one of the plural resistance elements Rk to switch the voltage. However, the present invention is not limited to this embodiment, and a voltage switching circuit which can switch the voltage by switching the resistor connected to the power supply can be broadly applied.

Furthermore, in the above embodiment, the electrical conductivity of water is detected, and the target current It is specified from the electrical conductivity of water. However, in place of the electrical conductivity of water, the resistance value corresponding to the reciprocal number of the electrical conductivity may be achieved to specify the target current It from the resistance value.

Still furthermore, for example, ozone ($O_3$) or hydrogen peroxide ($H_2O_2$) may be generated as active oxygen species. In this case, when platinum tantalum electrodes are used as the electrodes 47, 48, active oxygen species can be highly efficiently and stably generated from water in which ion species are rare.

At this time, at the anode, the reactions represented by the following chemical formulas (5) to (7) occur:

$$2H_2O \rightarrow 4H^+ + O_2 + 4e^- \tag{5}$$

$$3H_2O \rightarrow O_3 + 6H^+ + 6e^- \tag{6}$$

$$2H_2O \rightarrow O_3 + 4H^+ + 4e^- \tag{7}$$

Furthermore, at the cathode, the reactions represented by the following chemical formulas (8) and (9) occur, and $O^{2-}$ generated though electrode action and $H^+$ in solution are bonded with each other to generate hydrogen peroxide ($H_2O_2$):

$$4H^+ + 4e^- + (4OH^-) \rightarrow 2H_2 + (4OH^-) \tag{8}$$

$$O_2^- + e^- + 2H^+ \rightarrow H_2O_2 \tag{9}$$

In this construction, by supplying current to the electrodes, ozone ($O_3$) and hydrogen peroxide ($H_2O_2$) having strong sterilization power are generated, and electrolytic water containing ozone ($O_3$) and hydrogen peroxide ($H_2O_2$) can be generated. The concentration of ozone or hydrogen peroxide in this electrolytic water is adjusted to such a concentration that target virus, etc. can be inactivated, and air is passed through the gas-liquid contact member 53 supplied with the electrolytic water having this concentration, whereby target virus, etc. floating in the air can be inactivated. Furthermore, when odor components pass through the gas-liquid contact member 53, these components react with ozone or hydrogen peroxide in the electrolytic water to be ionized and soluble in water, so that the odor components are removed and deodorized.

Furthermore, the above embodiment adopts a water supply system based on the water supply tank 41 which can be freely inserted and taken out. However, in place of use of the water supply tank 41, a water pipe-distributing and supplying system in which a tap water pipe is connected to directly supply city water to the air filtering apparatus 1 may be used.

Still furthermore, in the above embodiment, electrolytic water is dropped to the gas-liquid contact member 53. However, the present invention is not limited to this embodiment, and electrolytic water may be sucked up by the gas-liquid contact member 53. In this case, for example, the lower edge portion of the gas-liquid contact member 53 is located at a lower position than the water level of electrolytic water in the water receiving tray 42 for stocking electrolytic water, the lower portion of the gas-liquid contact member 53 is immersed in the electrolytic water, and the electrolytic water is sucked up by using a so-called capillary phenomenon, whereby the electrolytic water is infiltrated into the gas-liquid contact member 53.

What is claimed is:

1. An air filtering apparatus in which power is supplied from a power supply to electrodes in an electrolytic bath to electrolyze water in the electrolytic bath and thus generate electrolytic water and the generated electrolytic water and air are supplied to a gas-liquid contact member to filter the air, comprising:
   a voltage varying unit that varies the voltage applied between the electrodes and includes a voltage switching unit for switching a power supply voltage, a voltage adjusting unit for adjusting the power supply voltage switched by the voltage switching unit and applying the adjusted voltage between the electrodes and a controller for controlling the voltage switching unit so that the power supply voltage is adjusted to a voltage nearest to the adjusted power supply voltage by the voltage adjusting unit.

2. The air filtering apparatus according to claim 1, wherein the voltage switching unit switches a resistor connected to the power supply, and outputs the voltage based on the switched resistor, thereby switching the power supply voltage. According to this construction, the power supply voltage is switched by switching the resistor, so that the construction of the voltage switching unit can be simplified.

3. The air filtering apparatus according to claim 2, wherein the voltage switching unit comprises plural resistance elements, and a switching unit for selectively connecting the plural resistance elements to the power supply under the control of the controller.

4. The air filtering apparatus according to claim 1, wherein the voltage adjusting unit adjusts the power supply voltage switched by the voltage switching unit through pulse width modulation.

5. The air filtering apparatus according to claim 1, wherein the controller has a detector for detecting the electrical conductivity or resistance value of water in the electrolytic bath, sets target current to flow between the electrodes on the basis of the detection result of the detector, and controls the voltage switching unit and the voltage adjusting unit so that current flowing between the electrodes is converged within a predetermined range based on the target current.

6. The air filtering apparatus according to claim 5, wherein the controller controls the voltage switching unit and the voltage adjusting unit so that the voltage applied between the electrodes is gradually varied when the current flowing between the electrodes is out of the predetermined range based on the target current and then kept to the voltage at the time point when the current flowing between the electrodes enters the predetermined range.

7. The air filtering apparatus according to claim 5, wherein the controller controls the voltage switching unit and the voltage adjusting unit so that the voltage applied between the electrodes is equal to the lowest voltage under a condition that the current flowing between the electrodes exceeds the target current and the difference between the current and the target current is equal to a predetermined value or more, and executes alarm processing insofar as the condition concerned is satisfied even after the control.

* * * * *